United States Patent [19]

Burke et al.

[11] Patent Number: 4,780,245
[45] Date of Patent: Oct. 25, 1988

[54] SOLUBILIZATION OF DIMETHYL POLYSILOXANES

[75] Inventors: John J. Burke, Farmington Hills; Robert R. Roelofs, Wyandotte, both of Mich.

[73] Assignee: BASF Corporation, Parsippany, N.J.

[21] Appl. No.: 841,165

[22] Filed: Mar. 19, 1986

[51] Int. Cl.$^4$ .............................................. B01J 13/00
[52] U.S. Cl. ............................. 252/312; 106/287.14; 514/938
[58] Field of Search .......................... 252/312, 8.554; 106/287.14; 514/938

[56] References Cited

U.S. PATENT DOCUMENTS 3,748,275 7/1973 Bernheim et al. .................. 252/312
4,384,974 5/1983 Guthauser ...................... 514/938 X
4,479,887 10/1984 Seibert ............................ 252/312 X Primary Examiner—John F. Terapane
Assistant Examiner—Virginia B. Caress
Attorney, Agent, or Firm—Bill C. Panagos

[57] ABSTRACT

The instant invention relates to liquid compositions useful in cosmetic applications comprising a polysiloxane selected from the group consisting of cyclic and non-cyclic dimethyl polysiloxanes and mixtures thereof, at least one nonionic polyoxyalkylene block copolymer, and water. This polyoxyalkylene copolymer is a cogeneric mixture of conjugated polyoxyalkylene compounds containing in their structure the residue of an active hydrogen-containing compound having from 2 to 4 carbon atoms, 2 to 4 active hydrogen atoms at least one hydrophobic oxyalkylene chain in which the oxygen-carbon atom ratio does not exceed 0.4 and at least one hydrophilic oxyalkylene chain in which the oxygen-carbon atom ratio is greater than 0.4 and water.

19 Claims, No Drawings

SOLUBILIZATION OF DIMETHYL POLYSILOXANES

BACKGROUND OF THE INVENTION

This invention relates to solubilized water insoluble dimethyl polysiloxanes including both the cyclic and the non-cyclic dimethyl polysiloxanes. The compositions of this invention are particularly useful in cosmetic applications.

The solubilization of common cosmetic oils into aqueous media has always been of interest to the cosmetic formulator. However, the number of chemical compounds available as recognized solubilizers and their range of functionality in this capacity remain quite limited. Consequently the cosmetic formulator has sought alternate emollient oils which have been chemically modified to achieve aqueous solubility. At times, either the aesthetics or the costs of using such oils have limited their use. At other times, no chemically modified oils are commercially available to fill the aesthetic requirements of a finished formulation.

Cyclic and non-cyclic dimethyl polysiloxanes provide a great number of unique aesthetic/tactile characteristics, i.e., outstanding lubricity, gloss and elegance in finished formulae. The cyclic polysiloxanes additionally provide lubricity without oily feel or tackiness. They are also warm and dry on application. Unfortunately they must be used in reasonably large amounts to achieve these effects, yet are incompatible in aqueous systems at those needed levels.

Accordingly, it is a purpose of the instant invention to provide for the solubilization of the water insoluble dimethyl polysiloxanes.

SUMMARY OF THE INVENTION

In accordance with the instant invention, it has been discovered that the above objects may be achieved with liquid compositions useful in cosmetic applications comprising a polysiloxane selected from the group consisting of cyclic and non-cyclic dimethyl polysiloxanes and mixtures thereof, at least one nonionic polyoxyalkylene block copolymer, and water. This polyoxyalkylene copolymer is a cogeneric mixture of conjugated polyoxyalkylene compounds containing in their structure the residue of an active hydrogen-containing compound having from 2 to 4 carbon atoms, 2 to 4 active hydrogen atoms, at least one hydrophobic oxyalkylene chain in which the oxygen-carbon atom ratio does not exceed 0.4 and at least one hydrophilic oxyalkylene chain in which the oxygen-carbon atom ratio is greater than 0.4.

DETAILED DESCRIPTION OF THE INVENTION

The non-cyclic dimethyl polysiloxanes that may be solubilized are mixtures of fully methylated linear siloxane polymers end blocked with trimethylsiloxy units and believed to have the following general formula:

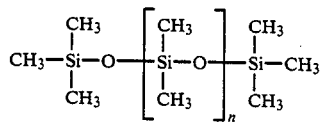

wherein n is sufficient to render the viscosity in the range of 5 to 1000 centistokes.

The cyclic dimethyl polysiloxanes that may be solubilized are either octamethyl-cyclotetrasiloxane (tetramer or "D4" type), decamethyl-cyclopentasiloxane (pentomer or "D4" type) or blends of the two, and are believed to have the following general formulas:

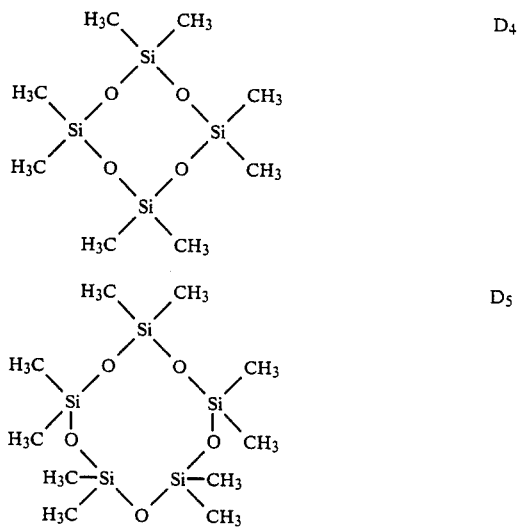

The composition of the instant invention comprises by weight about 20 to 80 percent of the dimethyl polysiloxane, about 5 to 50 percent of the nonionic polyoxyalkylene block copolymer, and about 5 to 60 percent water. The polyoxyalkylene copolymer employed for solubilizing the dimethyl polysiloxane is a cogeneric mixture of conjugated polyoxyalkylene compounds containing in their structure, oxypropylene groups, oxyethylene groups, and the residue of an active hydrogen containing compound. The term "cogeneric mixture" used herein is a term that has been coined to designate a series of closely related homologues that are obtained by condensing a plurality of alkylene oxide units with a reactive hydrogen compound (see U.S. Pat. No. 2,549,438, particularly the sections beginning at column 12, line 40). This expression is well known to those skilled in the art as can be seen from U.S. Pat. Nos. 2,677,700; 2,674,619; and 2,979,528.

The active hydrogen containing compound also referred to herein as an initiator preferably has about 2 to 4 carbon atoms, and about 2 to 4 active hydrogen atoms. Such initiators include ethylene glycol, propylene glycol, butylene glycol, and ethylenediamine.

In one preferred embodiment of this invention, the oxyalkylene compounds are those of the type disclosed in U.S. Pat. Nos. 2,674,619; 2,979,528; and 2,677,700 prepared by first oxypropylating an active hydrogen containing initiator compound, preferably propylene glycol or ethylene diamine and subsequently oxyethylating the resulting compound as more completely described in said patents, incorporated herein by reference. In such compounds the polyoxypropylene groups are present in polyoxypropylene chains that are attached to the initiator nucleus at the site of the reactive hydrogen atoms thereby constituting a polyoxypropylene polymer. The oxyethylene groups are attached to the polyoxypropylene polymer in oxyethylene chains.

The oxyalkylene compounds may also be those of the type disclosed in U.S. Pat. No. 3,036,118 prepared by first oxyethylating an active hydrogen containing initiator compound, preferably ethylene glycol, and subsequently oxypropylating the resulting compound as more completely described in said patent, incorporated herein by reference. In such compounds the polyoxyethylene groups are present in polyoxyethylene chains that are attached to the initiator nucleus at the site of the reactive hydrogen atoms thereby constituting a polyoxyethylene polymer. The oxypropylene groups are attached to the polyoxyethylene polymer in oxypropylene chains. In all such polymers oxypropylene chains optionally but advantageously contain small amounts of ethylene oxide and the oxyethylene chains optionally but advantageously contain small amounts of other alkylene oxides such as propylene oxide and butylene oxide. These polyoxyalkylene compounds are believed to correspond to the formulas:

$$HO(C_2H_4O)_m(C_3H_6O)_n(C_2H_4O)_mH \quad (I)$$

and $$HO(C_3H_6O)_n(C_2H_4O)_m(C_3H_6O)_nH \quad (II)$$

Wherein n has a value such that the molecular weight of the polyoxypropylene hydrophobic base is about 1200 to 4000 in formula I and 2500 to 4000 in formula II and m has a value such that the oxyethylene content of the molecule is from about 10 to 30 weight percent.

It is further to be noted that when molecular weight is stated in this specification and claims, unless otherwise noted, there is meant the average theoretical molecular weight which equals the total of the grams of the alkylene oxide employed per mole of reactive hydrogen compound. It is well recognized in the field of alkylene oxide chemistry that the polyoxyalkylene compositions one obtains by condensing an alkylene oxide with a reactive hydrogen compound are actually mixtures of compounds rather than a single molecular compound. The mixture contains closely related homologues wherein the statistical average number of oxyalkylene groups equals the number of moles of the alkylene oxide employed and the individual members in the mixtures contain varying numbers of oxyalkylene groups. Accordingly, as already noted, the oxypropylene chains optionally but advantageously contain small amounts of ethylene oxide and the oxyethylene chains optionally but advantageously contain small amounts of alkylene oxides such as propylene oxide. Thus, the compositions of this invention are mixtures of compounds which are defined by molecular weight of the polyoxypropylene chains and weight percent of oxyethylene groups.

The polyoxyalkylene compositions may also be compounds as described in U.S. Pat. No. 2,979,528, incorporated herein by reference. These compositions are prepared in much the same way as the polyoxyalkylene compounds described above. However, instead of ethylene glycol or propylene glycol as an initiator, a reactive hydrogen compound containing nitrogen is utilized. Ethylene diamine is the preferred nitrogen-containing reactive hydrogen compound.

Useful nitrogen-containing nonionic surfactants are mixtures of conjugated polyoxyethylene polyoxypropylene compounds based on a nitrogen-containing reactive hydrogen compound wherein chains of oxypropylene groups having a defined molecular weight are attached to the nucleus of the reactive hydrogen compound at the sites of the hydrogen atoms and wherein the chains of oxyethylene groups are attached to opposite end of the oxypropylene chains. The compositions are prepared by condensing propylene oxide with a nitrogen-containing reactive hydrogen compound, preferably ethylenediamine and subsequently condensing ethylene oxide with the propylene oxide-reactive hydrogen compound. The collective molecular weight of the oxypropylene chains attached to the nitrogen-containing reactive hydrogen compound must be at least about 500 and can range up to about 2500 or higher. The weight percent oxyethylene groups is about 30 to 50. These compounds are believed to have the following formula:

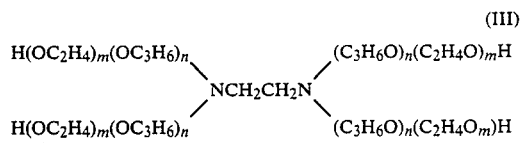

wherein n has a value such that the molecular weight of all the polyoxypropylene hydrophobic groups is about 500 to 2500 and m has a value such that the oxyethylene content of the molecule is from about 30 to 50 weight percent.

Accordingly, the preferred composition of this invention comprises by weight about 20 to 80 percent polysiloxanes selected from the group consisting of cyclic and noncyclic dimethyl siloxanes and mixtures thereof, about 5 to 50 percent of a nonionic polyoxyalkylene polymer selected from the group consisting of those which correspond to the formulas:

$$HO(C_2H_4O)_m(C_3H_6O)_n(C_2H_4O)_mH \quad (I)$$

and $$HO(C_3H_6O)_n(C_2H_4O)_m(C_3H_6O)_nH \quad (II)$$

wherein n has a value such that the molecular weight of the polyoxypropylene hydrophobic base is about 1200 to 4000 in formula I and 2500 to 4000 in formula II and m has a value such that the oxyethylene content of the molecule is from about 10 to 30 weight percent and mixtures thereof, and those which correspond to the formula

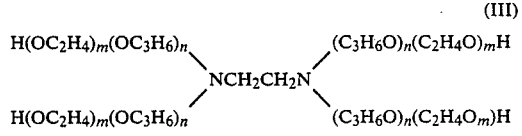

wherein n has a value such that the molecular weight of all the polyoxypropylene hydrophobic groups is about 500 to 2500 and m has a value such that the oxyethylene content of the molecule is from about 30 to 50 weight percent and mixtures thereof, and 5 to 60 percent water.

While the above formulas tend to show oxyethylene chains and the oxypropylene chains as if they were pure oxyethylene or oxypropylene, it is to be understood that the above representations include such compounds where, as stated above, the oxyethylene groups may contain small amounts of oxypropylene groups and the oxypropylene groups may contain small amounts of oxyethylene groups which results from the way such products are made. Also initiators other than propylene glycol or ethylene glycol, e.g. butylene glycol, may be employed to produce these compounds. The initiator represents a very small percentage of the total molecular weight of the compound and has very little if any effect on the properties. Accordingly, while the above formulas do not show compounds from initiators other than ethylene glycol or propylene glycol or ethylene diamine, as the case may be, such formulas are defined herein to include such compounds employing initiators other than ethylene glycol or propylene glycol or ethylene diamine.

In a preferred embodiment of the invention, the nonionic polyoxyalkylene component is a mixture of the compound of formula III above with a compound of formula I or II or mixture of both. The preferred mixture comprises a mixture of the compound of formula I and/or II above with that of formula III in a weight ratio of 2:1 to 1:2.

The preferred method of preparing the composition of the instant invention is to premix the polyoxyalkylene polymers with water followed by the addition of the polysiloxane. An alternate mode is to premix the polysiloxane with the polyoxyalkylene polymer followed by addition of the water. A third procedure is to premix the water and polysiloxane and later add the polyoxyalkylene polymer.

The invention is illustrated by the following specific examples, which are to be taken as illustrative and not in a limiting sense. Throughout the specification and claims parts are by weight unless otherwise specifically indicated, and temperatures are in degrees centigrade.

In the following examples the nonionic polyoxyalkylene copolymers are indicated in Table I and II under the heading "Nonionic" and may be defined as follows.

Nonionic No. 1 defines a block copolymer which is the polyoxyethylene adduct of a polyoxypropylene hydrophobic base. The molecular weight of the hydrophobic base is about 2100 and the oxyethylene content is about 33 percent by weight of the molecule.

Nonionic No. 2 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 950 and the oxyethylene content is about 10 weight percent of the molecule.

Nonionic No. 3 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 950 and the oxyethylene content is about 50 weight percent of the molecule.

Nonionic No. 4 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 1200 and the oxyethylene content is about 20 weight percent of the molecule.

Nonionic No. 5 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 1200 and the oxyethylene content is about 30 weight percent of the molecule.

Nonionic No. 6 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 1200 and the oxyethylene content is about 40 weight percent of the molecule.

Nonionic No. 7 defines a block copolymer which is the polyoxyethylene adduct of a polyoxypropylene hydrophobic base, i.e., comprises polyoxyethylene groups at both ends of a polyoxypropylene base as per formua I above. The molecular weight of the hydrophobic base is about 1750 and the oxyethylene content is about 10 weight percent of the molecule.

Nonionic No. 8 defines a block copolymer which is the polyoxyethylene adduct of a polyoxypropylene hydrophobic base. i.e., comprises polyoxyethylene groups at both ends of a polyoxypropylene base as per formula I above. The molecular weight of the hydrophobic base is about 1750 and the oxyethylene content is about 20 weight percent of the molecule.

Nonionic No. 9 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 1750 and the oxyethylene content is about 30 weight percent of the molecule.

Nonionic No. 10 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 1750 and the oxyethylene content is about 40 weight percent of the molecule.

Nonionic No. 11 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 1750 and the oxyethylene content is about 50 weight percent of the molecule.

Nonionic No. 12 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 2050 and the oxyethylene content is about 20 weight percent of the molecule.

Nonionic No. 13 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 2250 and the oxyethylene content is about 10 weight percent of the molecule.

Nonionic No. 14 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 2250 and the oxyethylene content is about 40 weight percent of the molecule.

Nonionic No. 15 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 2250 and the oxyethylene content is about 50 weight percent of the molecule.

Nonionic No. 16 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 2750 and the oxyethylene content is about 20 weight percent of the molecule.

Nonionic No. 17 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 3250 and the oxyethylene content is about 10 weight percent of the molecule.

Nonionic No. 18 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 3250 and the oxyethylene content is about 30 weight percent of the molecule.

Nonionic No. 19 defines a block copolymer which is the polyoxyethylene adduct of a polyoxypropylene hydrophobic base, i.e., comprises polyoxyethylene groups at both ends of a polyoxypropylene base as per formula I above. The molecular weight of the hydrophobic base is about 4000 and the oxyethylene content is about 20 weight percent of the molecule.

Nonionic No. 20 defines a block copolymer which is the polyoxypropylene adduct of a polyethylene base, i.e., comprises polyoxypropylene groups at both ends of a polyoxyethylene base at as per formula II above. The molecular weight of the polyoxypropylene groups is about 1000 and the oxyethylene content is about 50 weight percent of the molecule.

Nonionic No. 21 defines a block copolymer which is the polyoxypropylene adduct of a polyethylene base, i.e., comprises polyoxypropylene groups at both ends of a polyoxyethylene base as per formula II above. The molecular weight of the polyoxypropylene groups is about 2200 and the oxyethylene content is about 40 weight percent of the molecule.

Nonionic No. 22 defines a block copolymer which is the polyoxypropylene adduct of a polyethylene base, i.e., comprises polyoxypropylene groups at both ends of a polyoxyethylene base as per formula II above. The molecular weight of the polyoxypropylene group is about 2500 and the oxyethylene content is about 10 weight percent of the molecule.

Nonionic No. 23 defines a block copolymer which is the polyoxypropylene adduct of a polyethylene base, i.e., comprises polyoxypropylene groups at both ends of a polyoxyethylene base as per formula II above. The molecular weight of the polyoxypropylene groups is about 3100 and the oxyethylene content is about 10 weight percent of the molecule.

Nonionic No. 24 defines a block copolymer which is the polyoxypropylene adduct of a polyethylene base, i.e., comprises polyoxypropylene groups at both ends of a polyoxyethylene base as per formula II above. The molecular weight of the polyoxypropylene groups is about 3100 and the oxyethylene content is about 20 weight percent of the molecule.

Nonionic No. 25 defines a block copolymer which is the polyoxyethylene adduct of a polyoxypropylene ethylene diamine condensate of the type of formula III above. The oxypropylene hydrophobic base has a molecular weight of about 1000 and the oxyethylene content is about 40 weight percent of the molecule.

Nonionic No. 26 defines a block copolymer which is the polyoxyethylene adduct of a polyoxypropylene ethylene diamine condensate of the type of formula III above. The oxypropylene hydrophobic base has a molecular weight of about 2000 and the oxyethylene content is about 40 weight percent of the molecule.

Nonionic No. 27 defines a block copolymer which is the polyoxyethylene adduct of a polyoxypropylene ethylene diamine condensate of the type of formula III above. The oxypropylene hydrophobic base has a molecular weight of about 3000 and the oxyethylene content is about 10 weight percent of the molecule.

Nonionics 28–44 were polyoxyethylene adducts of a polyoxypropylene-ethylene diamine condensate of the type of formula III above. Nonionics 28, 29, and 30 had an oxypropylene group molecular weight of about 3000 with percentages of oxyethylene groups of 20, 40, and 70 weight percent, respectively. Nonionics 31, 32, and 33 were similar except that the molecular weight of the polyoxypropylene hydrophobes was about 4000 and the percentage of oxyethylene groups was 10, 40 and 80 weight percent of the molecule, respectively.

Nonionics 34–44 were similar with the exception that 34–36 had oxypropylene molecular weights of about 5000; 37–40 had oxypropylene molecular weights of about 6000; and 41–44 had oxypropylene molecular weights of about 7000. Nonionics 34–36 had percent oxyethylene groups of 10, 40 and 70 percent, respectively. Nonionics 37–40 had oxyethylene group molecular weights of 10, 20, 40, and 70, respectively. Nonionics 41–44 had percent oxyethylene groups of 10, 20, 40, and 80 percent, respectively.

Nonionic No. 45 was a polyoxypropylene adduct of a polyoxyethylene-ethylene diamine condensate of the type of formula III above wherein the oxypropylene groups had a molecular weight of about 5000 and the oxyethylene content was about 20 weight percent of the molecule.

EXAMPLES 1–28

Tertiary mixtures of water and each of the nonionics 1–44 were made with each of the following polysiloxanes.

These included both cyclic and noncyclic polysiloxanes. The cyclic polysiloxanes were all mixtures of the D-4 and D-5 cyclic polysiloxanes. the formulas of which are set forth earlier in this application. More specifically a mixture of 5 percent D-4 and 95 percent D-5 polysiloxane sold under the designation VS-7158 and two compositions which were mixtures of 95 percent D-4 and 5 percent D-5 sold under the designations VS-7207 and VS-7349, all three by Union Carbide; a 5 percent D-4, 95 percent D-5 composition sold under the designation SF-1202; and a 95 percent D-4, 5 percent D-5 mixture sold under the designation SF-1173, both by General Electric; a 25 percent D-4, 75 percent D-5 composition sold under the designation DC-345 and a 10 percent D-4, 90 percent D-5 composition sold under the designation DC-344, both by Dow Corning; a 10 percent D-4, 90 percent D-5 composition sold under the designation SWS-03314; a 20 percent D-4, 80 percent D-5 composition sold under the designation Siloxane 251, and a 95 percent D-4, 5 percent D-5 composition sold under the designation Siloxane 250, all these by SWS Silicones.

The noncyclic polysiloxanes consisted of three compounds sold under the name Silicone 200 fluid by Dow Corning, having respective viscosities of 10, 100, and 350, a Dow Corning compound sold under the designation Silicone 225 fluid having a viscosity of 200 centistokes; three compounds sold under the designation SF-96 fluid by General Electric having respectively 100, 350 and 1000 centistokes viscosity; a compound sold under the designation SWS-101 fluid by SWS Silicones having a viscosity of 5 centistokes; a compound sold under the designations F-221 fluid by SWS having a viscosity of 0.65 centistokes; and a compound sold under the designation Silicone L-45 fluid by Union Carbide having a viscosity of 350 centistokes.

The amount of water in each mixture was 10 percent. Separate mixtures of each of the above polysiloxanes and each nonionic were made at weight ratios of polyoxyalkylene copolymer to polysiloxane of 1:2, 1:1, and 2:1. More specifically, tertiary mixtures were made from each nonionic, 1–44, with each of the polysiloxanes in each of the ratios. In other words, for each nonionic listed below, 60 mixtures were made up. The mixtures were observed after 5 minutes and the results are set forth in Table I. Since the results for each of the 60 mixtures from a given nonionic, for example Nonionic No. 1, were all the same, only one indication is made in the result column for each nonionic rather than 60. The results are indicated in Table I below by numerals and letters which are defined as follows:

| | |
|---|---|
| 2 = 2 phase separation | C = top layer creaming |
| 3 = 3 phase separation | H = hazy aqueous phase |
| U = uniform emulsion | |

TABLE I

| Example | Nonionic Copolymer | Results | Example | Polyoxyalkylene Copolymer | Results |
|---|---|---|---|---|---|
| 1 | 1 | 2 | 16 | 16 | 2C |
| 2 | 2 | 2 | 17 | 17 | 2C |
| 3 | 3 | 2 | 18 | 18 | 2 |
| 4 | 4 | 2H | 19 | 19 | U |
| 5 | 5 | 2 | 20 | 20 | 2 |
| 6 | 6 | 2C | 21 | 21 | 2 |
| 7 | 7 | 3 | 22 | 22 | 3 |
| 8 | 8 | U | 23 | 23 | 3 |
| 9 | 9 | 2H | 24 | 24 | U |
| 10 | 10 | 2C | 25 | 25 | U |
| 11 | 11 | 2C | 26 | 26 | 2C |
| 12 | 12 | U | 27 | 27 | 3 |
| 13 | 13 | U | 28 | 28–44 | 2 |
| 14 | 14 | 2H | | | |
| 15 | 15 | 2 | | | |

EXAMPLES 29–74

Mixtures were made up as described above for Examples 1–30 with the exception that rather than using single block copolymers, blends of a copolymer of formula I or II with a copolymer of formula III were substituted therefor. Each blend was mixed in a 1.5:1, 1:1 and 1:1.5 weight ratio with each of the above-listed siloxanes. Thus, there were 60 mixtures made from each copolymer blend. However, as with previous examples, all 60 mixtures using a given copolymer blend had the same results. These results are indicated in Table II below by numerals and letters which are defined as follows.

2 = two-phase separation
H = hazy but uniform solution
C = clear, uniform solution

TABLE II

| | Nonionic Blend | | |
|---|---|---|---|
| Example | Formula I or II | Formula III | Results |
| 29 | 3 | 25 | 2 |
| 30 | 4 | 25 | C |
| 31 | 5 | 25 | H |
| 32 | 6 | 25 | 2 |
| 33 | 7 | 25 | 2 |
| 34 | 8 | 25 | C |
| 35 | 9 | 25 | H |
| 36 | 10 | 25 | 2 |
| 37 | 11 | 25 | 2 |
| 38 | 12 | 25 | C |
| 39 | 13 | 25 | H |
| 40 | 14 | 25 | 2 |
| 41 | 15 | 25 | 2 |
| 42 | 18 | 25 | 2 |
| 43 | 19 | 25 | 2 |
| 44 | 24 | 25 | H |
| 45 | 3 | 26 | 2 |
| 46 | 4 | 26 | H |
| 47 | 5 | 26 | H |
| 48 | 6 | 26 | 2 |
| 49 | 7 | 26 | 2 |
| 50 | 8 | 26 | C |
| 51 | 9 | 26 | H |
| 52 | 10 | 26 | 2 |
| 53 | 11 | 26 | 2 |
| 54 | 12 | 26 | C |
| 55 | 13 | 26 | H |
| 56 | 14 | 26 | 2 |
| 57 | 18 | 26 | 2 |
| 58 | 19 | 26 | 2 |
| 59 | 3 | 45 | 2 |
| 60 | 4 | 45 | 2 |
| 61 | 5 | 45 | 2 |
| 62 | 6 | 45 | 2 |
| 63 | 7 | 45 | 2 |
| 64 | 8 | 45 | 2 |
| 65 | 9 | 45 | 2 |
| 66 | 10 | 45 | 2 |
| 67 | 11 | 45 | 2 |
| 68 | 12 | 45 | 2 |
| 69 | 13 | 45 | 2 |
| 70 | 14 | 45 | 2 |
| 71 | 15 | 45 | 2 |
| 72 | 18 | 45 | 2 |
| 73 | 19 | 45 | 2 |
| 74 | 24 | 45 | 2 |

While there has been shown and described herein certain embodiments of the present invention, it is intended that there be covered as well any change or modification therein which may be made without departing from the spirit and scope thereof.

The embodiments of the invention in which an exclusive property or privilege is claimed are defined as follows:

1. A liquid emulsion composition comprising:
   polysiloxanes selected from the group consisting of cyclic dimethyl polysiloxanes, non-cyclic dimethyl polysiloxanes, and mixtures thereof
   polyoxyalkylene polymer selected from the group consisting of
   those which correspond to the formulas:

$$HO(C_2H_4O)_m(C_3H_6O)_n(C_2H_4O)_mH \qquad (I)$$

and $$HO(C_3H_6O)_n(C_2H_4O)_m(C_3H_6O)_nH \qquad (II)$$

wherein n has a value such that the molecular weight of the polyoxypropylene hydrophobic base is about 1200 to 4000 for formula I and 2500 to 4000 for formula II, and m has a value such that the oxyethylene content of the molecule is from about 10 to 30 weight percent, and mixtures thereof, and those which correspond to the formula:

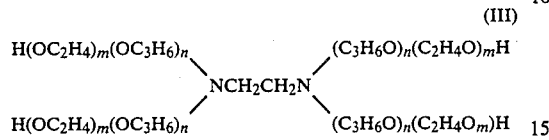
(III)

wherein n has a value such that the molecular weight of all the polyoxypropylene hydrophobic groups is about 500 to 2500, and m has a value such that the oxyethylene content of the molecule is from about 30 to 50 weight percent and mixtures thereof and water.

2. The composition of claim 1 wherein said polyoxyalkylene polymer is the polymer designated by formula I.

3. The composition of claim 1 wherein said polyoxyalkylene polymer is the polymer designated by formula II.

4. The composition of claim 1 wherein said polyoxyalkylene polymer is the polymer which corresponds to formula III.

5. The composition of claim 1 employing a blend of the polymer which corresponds to formula III with a polymer selected from the group consisting of those which correspond to formulae I and II and mixtures thereof.

6. The composition of claim 5 wherein the weight ratio of the polymer corresponding to formula III to that selected from the group consisting of the polymers II and I and mixtures thereof is from about 2:1 to 1:2.

7. The composition of claim 1 comprising by weight about 20 to 80 percent of said polysiloxanes, 5 to 50 percent of said polyoxyalkylene polymer and about 5 to 60 percent water.

8. The composition of claim 2 comprising by weight about 20 to 80 percent of said polysiloxanes, about 5 to 50 percent of said polyoxyalkylene polymer and about 5 to 60 percent water.

9. The composition of claim 3 comprising by weight about 20 to 80 percent of said polysiloxanes, about 5 to 50 percent of said polyoxyalkylene polymer and about 5 to 60 percent water.

10. The composition of claim 4 comprising by weight about 20 to 80 percent of said polysiloxanes, about 5 to 50 percent of said polyoxyalkylene polymer and about 5 to 60 percent water.

11. A process for solubilizing dimethyl polysiloxanes comprising adding thereto polyoxyalkylene polymer selected from the group consisting of:

those which correspond to the formulas

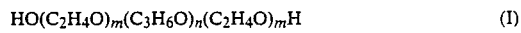
(I)

and

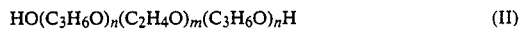
(II)

wherein n has a value such that the molecular weight of the polyoxypropylene hydrophobic base is about 1200 to 4000 for formula I and 2500 to 4000 for formula II, and m has a value such that the oxyethylene content of the molecule is from about 10 to 30 weight percent, and mixtures thereof and those which correspond to the formula:

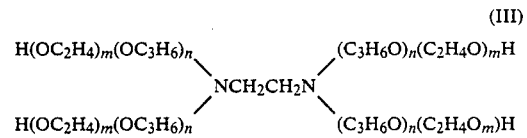
(III)

wherein n has a value such that the molecular weight of all the polyoxypropylene hydrophobic groups is about 500 to 2500, and m has a value such that the oxyethylene content of the molecule is from about 30 to 50 weight percent and mixtures thereof, and water.

12. The process of claim 11 wherein the polyoxyalkylene polymer is mixed with water followed by addition of the polysiloxane.

13. The process of claim 11 wherein the polysiloxane is mixed with the polyoxyalkylene polymer followed by addition of water.

14. The process of claim 11 wherein the polysiloxane is mixed with water after which the polyoxyalkylene polymer is added.

15. The process of claim 11 wherein the polyoxyalkylene polymer component is a blend of the polyoxyalkylene polymer of formula III with the polyoxyalkylene polymer selected from the group consisting of those represented by formula I and formula II and mixtures thereof in proportion by weight of 2:1 to 1:2.

16. The process of claim 15 wherein the amount of said polysiloxane is about 20 to 80 percent and the amount of polyoxyalkylene polymer is about 5 to 50 percent.

17. The process of claim 16 wherein the polyoxyalkylene polymer is mixed with about 5 to 60 percent water followed by addition of the polysiloxane.

18. The process of claim 16 wherein the polysiloxane is mixed with the polyoxyalkylene polymer followed by addition of about 5 to 60 percent water.

19. The process of claim 16 wherein the polysiloxane is mixed with about 5 to 60 percent water after which the polyoxyalkylene polymer is added.

* * * * *